United States Patent [19]

Andrews

[11] Patent Number: 5,569,461
[45] Date of Patent: Oct. 29, 1996

[54] TOPICAL ANTIMICROBIAL COMPOSITION AND METHOD

[75] Inventor: Jeffrey F. Andrews, Stillwater, Minn.

[73] Assignee: Minnesota Mining and Manufacturing Company, Saint Paul, Minn.

[21] Appl. No.: 384,942

[22] Filed: Feb. 7, 1995

[51] Int. Cl.$^6$ .................................................. A61K 9/10
[52] U.S. Cl. ........................................ 424/405; 424/400
[58] Field of Search .................................. 424/405, 401, 424/426, 400; 514/552

[56] References Cited

U.S. PATENT DOCUMENTS

| | | | |
|---|---|---|---|
| 3,806,615 | 4/1974 | Frankenfeld et al. | 426/328 |
| 4,002,775 | 1/1977 | Kabara | 426/532 |
| 4,067,997 | 1/1978 | Kabara | 424/312 |
| 4,160,820 | 7/1979 | Wagenknecht et al. | 424/48 |
| 4,189,481 | 2/1980 | Kabara | 424/248.54 |
| 4,299,852 | 11/1981 | Ueno et al. | 426/266 |
| 4,363,763 | 12/1982 | Peterson | 260/410.7 |
| 4,469,635 | 9/1984 | Peterson | 260/404 |
| 4,722,941 | 2/1988 | Eckert et al. | 514/784 |
| 4,921,694 | 5/1990 | Hoppe et al. | 424/65 |
| 4,938,953 | 7/1990 | Pena et al. | 424/70 |
| 5,093,140 | 3/1992 | Watanabe | 426/326 |
| 5,208,257 | 5/1993 | Kabara | 514/552 |
| 5,219,887 | 6/1993 | Andrews et al. | 514/552 |
| 5,364,650 | 11/1994 | Guthery | 426/331 |
| 5,378,731 | 1/1995 | Andrews et al. | 514/552 |
| 5,380,756 | 1/1995 | Andrews et al. | 514/552 |

FOREIGN PATENT DOCUMENTS

| | | | |
|---|---|---|---|
| 0243145 | 10/1987 | European Pat. Off. | A61K 31/20 |
| 0244144 | 11/1987 | European Pat. Off. | A23L 3/34 |
| 0312519 | 4/1989 | European Pat. Off. | A23B 4/14 |
| 0530861A2 | 3/1993 | European Pat. Off. | A61K 31/20 |
| WO92/21320 | 10/1992 | WIPO | A61K 7/06 |
| WO95/07616 | 3/1995 | WIPO | A23B 4/10 |

OTHER PUBLICATIONS

CH 634 749 abstract, Feb. 28, 1983.
Abstract, Derwent Publication, JP 77–73621, Sep. 3, 1977.
Abstract, Derwent Publication, JP 76–84022, Sep. 22, 1976.
Abstract, Derwent Publication, JP 77–22781, Feb. 17, 1977.
Baker et al., "Antimicrobial Properties of Lauricidin in Mechanically Deboned Chicken, Minced Fish and Chicken Sausage", *J. of Food Safety*, 4(1982), pp. 177–184.
Bell et al., "The Efficacy of Nisin, Sorbic Acid and Monolaurin as Preservatives in Pasteurized Cured Meat Products", *Food Microbiology*, 4, 1987, pp. 277–283.
Kato et al., Abstract, "Combined Effect of Citric and Polyphosphoric Acid on the Antibacterial Activity of Monoglycerides", vol. 4, No. 6 (1976).
Kato et al., Abstract, "Combined Effect of Different Drugs on the Antibacterial Activity of Fatty Acids and Their Esters", vol. 3, No. 8 (1975).
Cunningham, "Methods of Preservation of Poultry Products", The Microbiology of Poultry Meat Products, Chapter 9, 1987, pp. 275–292.
Dychdala, "Acid–Anionic Surfactant Sanitizers", *Disinfection, Sterilization, and Preservation*, 2nd Edition, (16) pp. 319–323, 1977.
Hall et al., "Spice Extracts, Lauricidin, and Propylene Glycol as Inhibitors of Clostridium Botulinum in Turkey Frankfurter Slurries", *Poultry Science*, vol. 65(6), 1986, pp. 1167–1171.
Juven et al., "A Hot Acid Treatment for Eliminating Salmonella from Chicken Meat", *J. Milk Food Technol.*, vol. 37, No. 5 (1974), pp. 237–239.
Kabara, "GRAS Antimicrobial Agents for Cosmetic Products", *J. Soc. Cosmet. Chem.*, 31, 1–10 (1980).
Kabara, "Food–Grade Chemicals for Use in Designing Food Preservative Systems", *J. of Food Protection*, vol. 44, No. 8, (1981), pp. 633–647.
Kabara, "A New Preservative System for Food", *J. of Food Safety*, 4 (1982), pp. 13–25.
Kabara, "Medium–Chain Fatty Acids and Esters as Antimicrobial Agents", *Cosmetic and Drug Preservation*, (16), 1984, pp. 275–356.
Nakagaki et al., "Solubility and Hydrolysis Rate of 1–Monolaurin in Aqueous Solutions", *Yakugaku Zasshi*, vol. 90 (10) 1970, pp. 1310–1315.
Satkowski et al., Polyoxyethylene Esters of Fatty Acids, Chapter 5, pp. 142–174.
Schemmel et al., "Monolauirn as an Anticaries Agent", Chapter 4, Symposium on the Pharmacological Effect of Lipids, pp. 37–43.
Thomson et al., "Chlorine, Acid, and Heat Treatments to Eliminate Salmonella on Broiler Carcasses", *Poultry Science*, 55 (1976), pp. 1513–1517.
Wooley, "EDTA–tris Potentiation of Antimicrobial Agents", *Modern Veterinary Practice*, (1983), pp. 113–116.
Asami et al., U.S. Patent Application Serial No. 08/276,531 filed Jul. 18, 1994.

*Primary Examiner*—Thurman K. Page
*Assistant Examiner*—Sharon Howard
*Attorney, Agent, or Firm*—Gary L. Griswold; Walter N. Kirn; Paul W. Busse

[57] ABSTRACT

A topical composition and related method for disinfecting, cleansing, conditioning and treating skin using a propylene glycol monoester of capric or caprylic acid, a second propylene glycol monoester or capric and/or caprylic acid, a synergist, propylene glycol, a surfactant and a vehicle are provided.

7 Claims, No Drawings

TOPICAL ANTIMICROBIAL COMPOSITION AND METHOD

TECHNICAL FIELD

This invention relates generally to topical antimicrobial compositions and particularly to aqueous solutions that exhibit antimicrobial properties when topically administered.

BACKGROUND OF THE INVENTION

The use of topical antimicrobial compositions to help treat, prevent or control diseases of man and other animals is an integral part of modern medicine. Topical antimicrobial compositions are also used to help prevent the spread of disease from animals to man, from man to animals and between animals. For example, antimicrobial compositions are used to disinfect meat carcasses in order to prevent food poisoning in humans. They are used on the teats of dairy animals such as cows and goats to help prevent mastitis and to help reduce the numbers of bacteria on the teat skin that could get into the milk during the milking process. Antimicrobial compositions may also be used in udder washes and both pre-milking and post-milking teat dips.

Because of the potential for contamination of milk by antimicrobial compositions used on cows teats, it is desired to use antimicrobial compositions that are generally recognized as safe, GRAS, as determined by the U.S. Food and Drug Administration in order to assure that any residues that may get into the milk from such uses are not toxic. Examples of antimicrobial compositions that are GRAS listed are both monoesters of edible fatty acids and polyhydric alcohols such as monolaurin and short to medium chained saturated fatty acids such as caprylic, capric, and lauric acids. In particular, the glycerol monoester of lauric acid (glycerol monolaurate or monolaurin) in combination with a chelating agent such as lactic acid is reported to be an effective antimicrobial system.

For example, U.S. Pat. No. 5,219,887 discloses the use of monolaurin with lactic acid as an antifungal, antibacterial system in a medicated shampoo. U.S. Pat. No. 5,208,257 discloses combinations of monolaurin, caprylic and capric acids with lactic acid as an effective antimicrobial system. U.S. Pat. No. 5,364,650 discloses the use of caprylic acid, capric acid, and a chelating agent without any monoester being present as a germicidal system useful for disinfecting animal carcasses to be used for human consumption. The concentrations of caprylic acid and capric acid in this system are kept very low (50–1500 ppm) so that they are soluble in water without the aid of other solvents or solubilizing surfactants. Kabara, J., *Cosmetic and Drug Preservation*, pp. 275–356, 1984, reports the use of monoglycerides, chelating agents, and medium chain fatty acids and combinations of these chemicals used as antimicrobial compositions, generally as preservatives.

U.S. patent application Ser. No. 08/121,283 filed Sep. 14, 1993 and International application No. PCT/U.S. 94/09370 filed Aug. 17, 1994 disclose the use of propylene glycol monoesters of edible fatty acids in combination with acids or chelating agents and GRAS anionic surfactants as a germicidal system useful for disinfecting meat carcasses to be used for human consumption.

Briefly, these exemplified reports are generally concerned with the use of monoglycerides as antimicrobial compositions and there is no detailed report other than U.S. application 08/121,283 and the related International application No. PCT/U.S. 94/09370, of the use of propylene glycol monoesters as antimicrobial compositions.

SUMMARY AND DETAILED DESCRIPTION OF THE INVENTION

The present invention provides topical antimicrobial compositions and methods, especially provides concentrated antimicrobial compositions which are useful when applied to the teats and udders of dairy animals as udder and teat washes and as pre-milking teat skin sanitizing solutions (predips). The present invention exploits, in part, the discovery that certain propylene glycol mono fatty acid esters, for example propylene glycol monocaprylate and propylene glycol monocaprate, in combination with both acidic chelating agents and edible saturated fatty acids are surprisingly potent antimicrobial systems. A combination of all three ingredients in the presence of propylene glycol vehicle provides an advantageous result.

Furthermore, this invention provides concentrated antimicrobial systems which may be used as a combination udder wash and predip simply by varying the dilution rate of the concentrated antimicrobial system. Typically an udder wash is a mild sanitizing solution containing a small amount of germicide plus cleaning agents such as soaps or detergents whose principle purpose is to remove dirt, manure, and other debris that may be on the teats and udder prior to milking the cow. A predip, on the other hand, is a strong germidical solution which is used prior to milking to substantially reduce the population of pathogenic organisms on the teats that cause certain types of mastitis in dairy cows. The principle purpose of an udder wash is not to control or prevent disease in cattle, but to help ensure that no foreign material such as dirt, manure, bedding, etc., gets into the milk via the milking process.

Because of economic necessity, udder washes are sold as concentrates to be diluted on the farm just prior to use. They are generally used as dilution's of about 1 oz. (29.6 ml) to a gallon (3.785 liters) (128:1) to about 1 oz. (29.6 ml) to four gallons (15.14 liters) of water (512:1). Large amounts of germicidal agents are required to be present in the concentrates so that an antimicrobially active solution results when the product is diluted for use. In such concentrates, monoglycerides such as monolaurin were not suitable because of the very low solubility of these monoglycerides in aqueous solutions. Even when cosolvents and solubilizing surfactants were used to aid the solubility of the monoglycerides, these mixtures formed solid creams instead of desired liquid solutions. Such creams can not be accurately measured, diluted or mixed on the farm, thus the monoglycerides are not suitable for use in the present germicidal system.

This invention is a unique combination of both germicidal and cleaning agents that makes it possible for a single concentrated antimicrobial composition to be both an udder wash and a predip, depending on the dilution factor that is used. For example, a high dilution such as 128:1 or 256:1 is prepared for udder washing, and a stronger or lower dilution, such as 4:1 or 8:1 is prepared for predipping. The economic advantage of purchasing one product to do the job of two products is a clear advance in the practice of pre-milking udder and teat sanitation.

Formulations of the antimicrobial system of this invention include antimicrobial components, skin softening and moisturizing agents, as well as skin cleansing agents. As an option, dyes or fragrances may be added for desired cosmetic properties.

The preferred antimicrobial system is a combination of propylene glycol monocaprylate, a mixture of caprylic and capric acids and lactic acid.

The propylene glycol monoesters of caprylic, capric and lauric acids are liquids (as opposed to the monolaurin which is a solid waxy material) that may be concentrated to high active levels in aqueous solutions when proper cosolvents and solubilizing surfactants are included in the formulations. These may be used in a range of about 1% to about 20% by weight in the formulation. Preferably they are used in amounts of 1 to 10% by weight, and most preferably in amounts of 3 to 10% by weight. Thus, they are highly suitable germicidal agents for use in the predip—udder wash. Importantly, these propylene glycol monoesters exhibit minimal germicidal effects when used alone, but when they are formulated with acidic chelating agents or food grade phenols they then exhibit a broad range of antimicrobial activity. This synergistic combination of propylene glycol monoesters and acidic chelating agents and food grade phenols is active against gram-positive bacteria such as *Staphylococcus aureus* and gram-negative bacteria such as *Escherichia coli* and against yeasts and fungi such as *Candida albicans*.

The preferred propylene glycol monoester is propylene glycol monocaprylate. Alternatively, a combination of the monoesters propylene glycol monocaprate and propylene glycol monocaprylate may be used, or up to 3% by weight (of the total solution) of propylene glycol monolaurate may be substituted for either of the preferred propylene glycol esters. Amounts of glycerol monolaurate above 3% are problematical because it is difficult to keep such amounts in solution. The monocaprylate and monocaprate esters are preferred because it has been observed that they provide more antimicrobial activity per unit weight.

Mixtures of caprylic and capric acid (commercially available as a 60:40, weight:weight ratio) are known germicidal agents (Kabara, J., *Cosmetic and Drug Preservation*, pp. 275–304, 1984 and references therein). These acids have an additive germicidal effect when formulated with the propylene glycol monoesters of this invention and may be used in a range of about 5% to about 20% by weight. Preferably they are used in amounts of 5 to 15% by weight, and most preferably in amounts of 5 to 10% by weight.

A synergist is the third required component of the formulations of the invention. Suitable synergists include acidic chelating agents such as lactic acid, tartaric acid, adipic acid, succinic acid, citric acid, ascorbic acid, malic acid, acetic acid, sorbic acid, sodium acid pyrophosphate, acidic sodium hexametaphosphate, and ethylenediaminetetraacetic acid and its salts as well as food grade phenols such as butylated hydroxyanisole and butylated hydroxytoluene. Preferred synergists are lactic acid and butylated hydroxyanisole. Most preferred is lactic acid. The acidic chelating agents are used in amounts of 5 to 20% by weight, preferably 5 to 15% by weight and most preferably 10 to 15% by weight. Lactic acid is preferred partly because it also acts as a skin softening agent. The synergists may be used solely or in combination.

Alternative formulations using mixtures of propylene glycol monoesters of caprylic and capric acid as the antimicrobial compositions and a synergist such as lactic acid are substantially as effective formulations as those using one propylene glycol monoester, caprylic and/or captic acid and lactic acid, but these are not preferred for most uses because they are more expensive due to the greater cost of the propylene glycol monoesters as compared to the cost of capric and caprylic acids.

The vehicle used for the formulations of the invention may be any conventional liquid vehicle commonly used for topical treatment of human or animal skin which is water or solvents miscible with water. Propylene glycol, as mentioned above, is one suitable solvent which may be used to replace some or all of the water which is preferably used as the principle vehicle in the formulations.

The skin softening agents in this formulation which help prevent drying and chapping of the teat skin are lactic acid and propylene glycol, which may be used in a range of about 5% to about 80% by weight of the formulation. At least 5% by weight propylene glycol is needed in the formulations of the invention, although higher amounts can be used when it is used both as a softening agent and/or solvent. Its cost (as compared to water) will usually argue against using it to the exclusion of water as the vehicle.

Some examples of the skin cleansing agents useful in the invention are the polyoxyethylene polyoxypropylene block copolymer surfactants (Pluronic F-68 from BASF, Parsippany, N.J.), the sodium lauryl ether sulfate surfactants (Rhodapex ES-2 from Rhone-Poulenc, Cranbury, N.J.), and the dioctyl sodium sulfosuccinate surfactants (Gemtex SC-40, from Finetex, Inc., Spencer, N.C.). These surfactant and detergent agents aid in removing the dirt and organic soil from the teats and udder. Each of these agents may be used in a range of about 5% to about 20% by weight of the formulation. Other surfactants that are not irritating to skin, udders or teats and that do not inactivate the antimicrobial properties of the present invention could also be used in these formulations.

As an option, fragrances and dyes may be included in the formulation to enhance its cosmetic appeal and acceptance.

The following examples provide detailed embodiments of the invention. The examples are provided for illustrative purposes and should not be construed to limit the scope of the invention which is defined in the claims.

EXAMPLE 1: CONCENTRATED COMPOSITION

A preferred formulation for a concentrated combination udder wash—predip was as follows:

| COMPONENT | % Wt. |
| --- | --- |
| Propylene glycol monocaprylate | 3.0 |
| Caprylic/capric acids | 10.0 |
| Lactic acid USP | 10.0 |
| Pluronic F-68 | 10.0 |
| Rhodapex ES-2 | 10.0 |
| Gemtex SC-40 | 5.0 |
| Propylene glycol | 20.0 |
| FDC Yellow #6 Dye | 0.01 |
| Deionized water | 31.99 |

This concentrate was combined by the following procedure which was carried out at room (ambient) temperature.

1. Add the lactic acid to the water and mix for five minutes.
2. Add the Pluronic F-68 to step 1 and mix for 15 minutes.
3. Add the Rhodapex ES-2 to step 2 and mix for five minutes.
4. Add the Gemtex SC-40 to step 3 and mix for five minutes.
5. Add the propylene glycol to step 4 and mix for five minutes.
6. Add the caprylic/capric acids to step 5 and mix for five minutes.
7. Add the propylene glycol monocaprylate to step 6 and mix for five minutes.

8. Add the FDC Yellow No. 6 dye to step 7 and mix for 20 minutes.

A clear light orange liquid concentrate was produced. This concentrate was then diluted with water just prior to use. If it was being used as an udder wash it was diluted at 0.50 oz. (14.8 ml) of concentrate in enough water to make one gallon (3.785 liters) of ready-to-use udder wash (1:256) or at one oz. (29.6 ml) of concentrate in enough water to make one gallon (3.785 liters) of ready-to-use udder wash (1:128). If it was to be used as a predip, the concentrate is diluted at from one pint (0.473 liter) of concentrate plus enough water to make one gallon (3.785 liters) of predip (1:8) as well as up to one quart (0.946 liter) of concentrate plus enough water to make one gallon (3.785 liters) of predip (1:4).

This product was applied to the teats and udder in the same manner as existing separate udder washes and predips are applied. For example, when used as an udder wash it may be applied with a sprayer and then wiped off with individual paper or cloth towels. Or it may be applied directly to the teats with individual paper or cloth towels and then removed with a separate towel or cloth. When applied as a predip, it may be applied with a sprayer or with a dip cup. When used as a predip it must be allowed to remain on the teats for at least 30 seconds and preferably for at least one minute in order to allow enough contact time for the germicide to kill the bacteria on the teat skin.

The propylene glycol monocaprylate is supplied by Unichema International, Chicago, Ill. The capylic/capric acids (60:40, weight:weight ratio) are supplied by Salim Oleochemicals, Inc., Dublin, Ohio.

EXAMPLE 2: ANTIMICROBIAL ACTIVITY

A batch of the antimicrobial composition of Example 1 was tested for antimicrobial activity by the general method of the National Mastiffs Council test as described in the November, 1977, Proposed Guidelines to Determine Biocidal Activity within a Teat Dip Solution as a Modification of the Germicidal and Detergent Sanitizer Test Official Methods of Analysis, A.O.A.C. 12th Edition, Section 4.023–4.032, pp. 63–65, 1975, the disclosure of which is incorporated herein by reference. The results of this testing are shown in Table 1. The data in Table 1 are log reductions of bacterial colony forming units from original inoculum counts. These data clearly show that this composition was a highly effective bactericidal agent.

TABLE 1

Bacterial Kill-Rate Tests of Preferred Udder Wash-Predip Composition

| | 128:1 DILUTION | | | 256:1 DILUTION | | |
|---|---|---|---|---|---|---|
| | TIME | | | | | |
| TEST ORGANISM | 30 SEC | 60 SEC | 120 SEC | 30 SEC | 60 SEC | 120 SEC |
| Staphylococcus aureus | 5.44 | >5.98 | 5.89 | 3.90 | 5.84 | >5.98 |
| Streptococcus agalactiae | 3.89 | >4.04 | >4.04 | 3.65 | 3.88 | >4.04 |
| Streptococcus uberis | 5.40 | >5.50 | >5.50 | 5.44 | >5.50 | 5.40 |
| Escherichia coli | >5.71 | >5.71 | >5.71 | >5.71 | >5.71 | >5.71 |
| Pseudomonas aeruginosa | 5.69 | >6.00 | >6.00 | >6.00 | >6.00 | >6.00 |

EXAMPLE 3: SKIN IRRITATION

It is very important that products used on teat skin do not cause any irritation or drying to the teat skin and to the teat ends. Tests were run on three dairy farms to determine whether or not the composition of Example 1 caused any teat skin or teat end irritation or dryness. In these tests, half of each herd used this experimental udder wash and half used whatever udder wash the dairy farmer was currently using on his herd. The teat skin and teat end conditions were judged at the beginning, midpoint, and at the end of the trials. The observations made at the beginning, midpoint, and end of the trials showed that there was no irritation, dryness, or teat end damage caused by the composition of this invention.

EXAMPLE 4: ALTERNATIVE COMPOSITION WITH TWO MONOESTERS

The propylene glycol monoesters may be used in combination at high concentrations as illustrated in the following formulation:

| COMPONENTS | %/Wt. |
|---|---|
| Propylene glycol monocaprylate | 5.0 |
| Propylene glycol monocaprate | 5.0 |
| Lactic acid | 5.0 |
| Sodium lactate | 5.0 |
| Pluronic F-68 | 10.0 |
| Rhodapex ES-2 | 10.0 |
| Butylated hydroxy anisole | 2.0 |
| Propylene glycol | 15.0 |
| Deionized water | 43.0 |

The propylene glycol monocaprate was supplied by Unichema, International, Chicago, Ill. The butylated hydroxy anisole was supplied by SIGMA Chemical Co., St. Louis, Mo. The sodium lactate and lactic acid were supplied by Wilke International, Inc., Olathe, Kans. The propylene glycol was supplied by J.T. Baker, Inc., Phillipsburg, N.J.

In this example, the second propylene glycol monoester gives additive germicidal properties to the first monoester of the formulation and is used for this purpose in place of the caprylic/capric acids in Example 1.

EXAMPLE #5: ALTERNATIVE COMPOSITION WITH THREE MONOESTERS

The propylene glycol esters may be combined with the monoglyceride esters such as monolaurin to give a suitable antimicrobial system. However, the monolaurin must be preferably kept at concentrations of 2% by weight or less since at concentrations higher than this, unstable solutions with heavy amounts of precipitate are formed and are therefore unacceptable.

| COMPONENTS | % Wt. |
|---|---|
| Propylene glycol monocaprylate | 1.0 |
| Propylene glycol monocaprate | 1.0 |
| Glyceryl monolaurate | 1.0 |
| Lactic acid | 10.0 |
| Pluronic F-68 | 10.0 |
| Rhodapex ES-2 | 10.0 |
| Gemtex SC-40 | 5.0 |
| Propylene glycol | 20.0 |
| FDC Yellow #6 Dye | 0.01 |
| Deionized water | 41.99 |

The glyceryl monolaurate is supplied by Medchem, Inc., Okemos, Mich.

In this example, the antimicrobial effects of all three of the monoesters are additive. Thus, the addition of the propylene glycol monocaprate and of the monolaurin serve to take the place of the caprylic/capric acid in Example 1.

What is claimed is:

1. A topical antimicrobial composition comprising effective amounts of:
   a) a primary antimicrobial component selected from the group consisting of propylene glycol monoesters of caprylic and capric acids and
   b) one or more secondary antimicrobial component(s) selected from the group consisting of propylene glycol monoesters of lauric, caprylic and capric acids, capric and caprylic acids, and
   c) a synergist selected from the group consisting of acidic chelating agents and food grade phenols and
   d) propylene glycol,
   e) surfactant, and
   f) a vehicle.

2. A composition according to claim 1 wherein the secondary antimicrobial is a mixture of capric and caprylic acids.

3. A composition according to claim 1 wherein the acid chelating agents is selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate and ethylenediaminetetraacetic acid and salts thereof.

4. A composition according to claim 1 comprising propylene glycol monocaprylate, a caprylic/capric acid mixture, lactic acid, a surfactant, propylene glycol and a vehicle.

5. A concentrated aqueous solution suitable for use as either an udder wash or a predip comprising
   a) about 1–20% by weight of a primary antimicrobial component selected from the group consisting of propylene glycol monoesters of caprylic and capric acids and
   b) about 1–20% by weight of one or more secondary antimicrobial component(s) selected from the group consisting of propylene glycol monoesters of laurie, caprylic and capric acids, captic and caprylic acids, and
   c) about 5–20% by weight of a synergist selected from the group consisting of acidic chelating agents and food grade phenols and
   d) about 5–20% by weight of a surfactant, and
   e) about 5–80% by weight of propylene glycol.

6. A method for treating or preventing topical skin infection comprising contacting the skin with a composition according to claim 1.

7. A method for treating teats comprising the step of contacting the teats with a composition according to claim 1.

* * * * *

UNITED STATES PATENT AND TRADEMARK OFFICE
CERTIFICATE OF CORRECTION

PATENT NO.: 5,569,461

DATED: October 29, 1996

INVENTOR(S): Jeffrey F. Andrews

It is certified that error appears in the above-identified patent and that said Letters Patent is hereby corrected as shown below:

Col. 3, line 61, "captic" should read --capric--.

Col. 5, line 34, "Mastiffs" should read --Mastitis--.

Col. 8, line 15, "captic" should read --capric--.

Signed and Sealed this

Second Day of September, 1997

Attest:

BRUCE LEHMAN

Attesting Officer

Commissioner of Patents and Trademarks